(12) United States Patent
Steinhauser et al.

(10) Patent No.: US 9,969,833 B2
(45) Date of Patent: May 15, 2018

(54) COLD FLOW REDUCED POLYMERS WITH GOOD PROCESSING BEHAVIOUR

(71) Applicant: LANXESS Deutschland GmbH, Cologne (DE)

(72) Inventors: Norbert Steinhauser, Dormagen (DE); Thomas Gross, Wuelfrath (DE)

(73) Assignee: ARLANXEO Deutschland GmbH, Dormagen (DE)

( * ) Notice: Subject to any disclaimer, the term of this patent is extended or adjusted under 35 U.S.C. 154(b) by 2 days.

(21) Appl. No.: 14/786,692

(22) PCT Filed: Apr. 11, 2014

(86) PCT No.: PCT/EP2014/057426
§ 371 (c)(1),
(2) Date: Oct. 23, 2015

(87) PCT Pub. No.: WO2014/173707
PCT Pub. Date: Oct. 30, 2014

(65) Prior Publication Data
US 2016/0083495 A1 Mar. 24, 2016

(30) Foreign Application Priority Data
Apr. 24, 2013 (EP) ..................................... 13165215

(51) Int. Cl.
| | | |
|---|---|---|
| *C08F 236/14* | (2006.01) |
| *C08K 3/04* | (2006.01) |
| *C08K 3/36* | (2006.01) |
| *B60C 1/00* | (2006.01) |
| *C08C 19/25* | (2006.01) |
| *C08C 19/30* | (2006.01) |
| *C08C 19/36* | (2006.01) |
| *C08C 19/44* | (2006.01) |
| *C08G 77/14* | (2006.01) |
| *C08L 13/00* | (2006.01) |
| *C07F 7/08* | (2006.01) |
| *C07F 7/18* | (2006.01) |
| *C08K 5/18* | (2006.01) |

(52) U.S. Cl.
CPC .............. *C08F 236/14* (2013.01); *B60C 1/00* (2013.01); *B60C 1/0016* (2013.01); *C07F 7/0805* (2013.01); *C07F 7/1848* (2013.01); *C08C 19/25* (2013.01); *C08C 19/30* (2013.01); *C08C 19/36* (2013.01); *C08C 19/44* (2013.01); *C08G 77/14* (2013.01); *C08K 3/04* (2013.01); *C08K 3/36* (2013.01); *C08K 5/18* (2013.01); *C08L 13/00* (2013.01); *C08J 2347/00* (2013.01); *C08K 3/045* (2017.05)

(58) Field of Classification Search
CPC ........... C08F 236/14; C08K 3/36; C08K 3/04; C08K 5/18; C08K 2003/045; C08K 3/045; C08J 2347/00; C07F 7/0805; C07F 7/1848; B60C 1/0016; B60C 1/00; C08C 19/25; C08C 19/30; C08C 19/36; C08C 19/44; C08L 13/00; C08L 9/00; C08G 77/14
USPC .................... 524/342, 575; 525/332.6, 332.7
See application file for complete search history.

(56) References Cited

U.S. PATENT DOCUMENTS

| | | | |
|---|---|---|---|
| 2,635,109 A | 4/1953 | Sommer | |
| 3,242,129 A | 3/1966 | Wilder et al. | |
| 3,244,664 A | 4/1966 | Zelinski et al. | |
| 4,033,731 A | 7/1977 | Bargain et al. | |
| 4,185,042 A | 1/1980 | Verkouw | |
| 4,417,029 A | 11/1983 | Milkovich | |
| 4,465,809 A | 8/1984 | Smith | |
| 4,604,478 A * | 8/1986 | Juen ..................... | C07F 7/1896 556/438 |
| 4,616,069 A | 10/1986 | Watanabe et al. | |
| 4,788,313 A | 11/1988 | Chandra et al. | |
| 5,385,999 A | 1/1995 | D'Anvers et al. | |
| 5,416,168 A | 5/1995 | Willis et al. | |
| 5,625,017 A | 4/1997 | Morita et al. | |
| 5,665,829 A | 9/1997 | Shepherd et al. | |
| 5,792,820 A | 8/1998 | Lawson et al. | |
| 6,013,718 A | 1/2000 | Cabioch et al. | |
| 6,025,450 A | 2/2000 | Lawson et al. | |
| 6,333,375 B1 | 12/2001 | Nakamura et al. | |
| 6,344,524 B1 | 2/2002 | Robert et al. | |
| 6,365,668 B1 | 4/2002 | Scholl et al. | |
| 9,587,059 B2 | 3/2017 | Steinhauser | |
| 2005/0009979 A1 | 1/2005 | Tanaka et al. | |
| 2005/0203251 A1 | 9/2005 | Oshima et al. | |
| 2008/0308204 A1 | 12/2008 | Hogan et al. | |
| 2013/0281609 A1 | 10/2013 | Steinhauser et al. | |

FOREIGN PATENT DOCUMENTS

| | | |
|---|---|---|
| DE | 2653144 A1 | 5/1979 |
| JP | 62010137 | 1/1987 |
| JP | 2008063274 A2 | 3/2008 |

OTHER PUBLICATIONS

Franta, I., Elastomers and Rubber Compounding Materials, 1989, Elsevier, pp. 113-131.

(Continued)

*Primary Examiner* — Josephine L Chang

(57) ABSTRACT

Cold flow-reduced polymers having good processing characteristics have, at the ends of the polymer chains, a silane-containing carboxyl group of the formula (I)

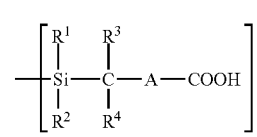

where $R^1$ and $R^2$ are the same or different and are each an H, alkyl, alkoxy, cycloalkyl, cycloalkoxy, aryl, aryloxy, alkaryl, alkaryloxy, aralkyl or aralkoxy; $R^3$ and $R^4$ are the same or different and are each an H, alkyl, cycloalkyl, aryl, alkaryl or aralkyl radical; A is a divalent organic radical.

11 Claims, 1 Drawing Sheet

(56) References Cited

OTHER PUBLICATIONS

Allen, Sir Geoffrey, Comprehensive Polymer Science, vol. 4, Part II (Pergamon Press Ltd., Oxford 1989), pp. 53-108.
Wolcott, J.M, et al., Journal of Organic Chemistry 1974, 39 (16), pp. 2420-2424.
Sibi, M. P., et al., Tetrahedron Letters 1995, 36 (35), pp. 6213-6216.
Linker, T., et al., Tetrahedron Letters 1996, 37 (46), pp. 8363-8366.
Shindo, M., Angewandte Chemie, International Edition 2004, 43 (1), pp. 104-106.
Meijerink, J. I., et al., "The influence of siloxane modifiers on the thermal expansion coefficient of epoxy resins", Polymer, Elsevier Science Publishers B.V., 1994, vol. 35, No. 1, pp. 179-186.
European Search Report from European Application No. 13165215, dated Feb. 13, 2014, three pages.

* cited by examiner

Extrusion profiles 3a-e and 7a-e of the tyre tread compositions 2a-e and 6a-e
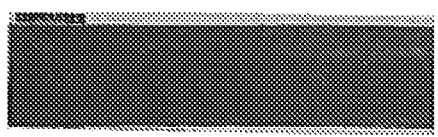
profile 3a
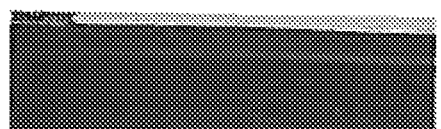
profile 7a
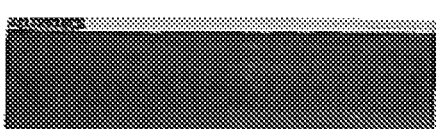
profile 3b
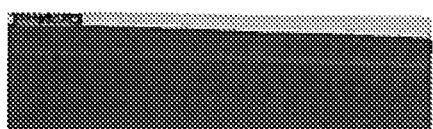
profile 7b
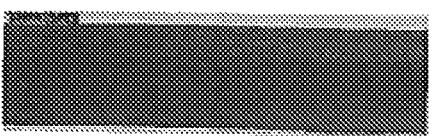
profile 3c
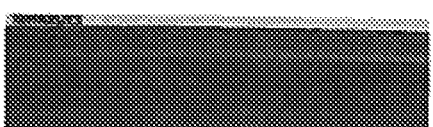
profile 7c
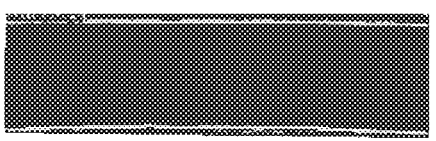
profile 3d
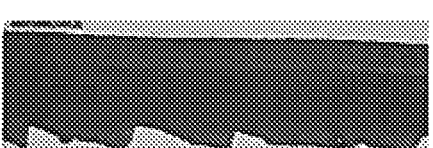
profile 7d
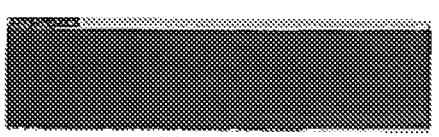
profile 3e
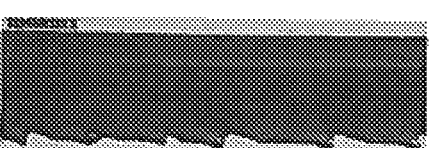
profile 7e

COLD FLOW REDUCED POLYMERS WITH GOOD PROCESSING BEHAVIOUR

The invention relates to cold flow-reduced, end group-functionalized polymers having good processing characteristics, and to the preparation and use thereof.

BACKGROUND INFORMATION

Important properties desirable in tyre treads include good adhesion on dry and wet surfaces, low rolling resistance and high abrasion resistance. It is very difficult to improve the skid resistance of a tyre without simultaneously worsening the rolling resistance and abrasion resistance. A low rolling resistance is important for low fuel consumption, and high abrasion resistance is a crucial factor for a long service life of the tyre.

Wet skid resistance and rolling resistance of a tyre tread depend largely on the dynamic/mechanical properties of the rubbers which are used in the blend production. To lower the rolling resistance, rubbers with a high resilience at higher temperatures (60° C. to 100° C.) are used for the tyre tread. On the other hand, for improving the wet skid resistance, rubbers having a high damping factor at low temperatures (0 to 23° C.) or low resilience in the range of 0° C. to 23° C. are advantageous. In order to fulfil this complex profile of requirements, mixtures of various rubbers are used in the tread. Usually, mixtures of one or more rubbers having a relatively high glass transition temperature, such as styrene-butadiene rubber, and one or more rubbers having a relatively low glass transition temperature, such as polybutadiene having a high 1,4-cis content or a styrene-butadiene rubber having a low styrene and low vinyl content or a polybutadiene prepared in solution and having a moderate 1,4-cis and low vinyl content, are used.

Anionically polymerized solution rubbers containing double bonds, such as solution polybutadiene and solution styrene-butadiene rubbers, have advantages over corresponding emulsion rubbers in terms of production of tyre treads with low rolling resistance. The advantages lie, inter alia, in the controllability of the vinyl content and of the associated glass transition temperature and molecular branching. In practical use, these give rise to particular advantages in the relationship between wet skid resistance and rolling resistance of the tyre.

Important contributions to energy dissipation and hence to rolling resistance in tyre treads result from free ends of the polymer chains and from the reversible buildup and degradation of the filler network formed by the filler used in the tyre tread mixture (usually silica and/or carbon black).

The introduction of functional groups at the end of the polymer chains and/or start of the polymer chains enables physical or chemical attachment of these ends and/or starts of the chains to the filler surface. This restricts the mobility thereof and hence reduces energy dissipation under dynamic stress on the tyre tread. At the same time, these functional groups can improve the dispersion of the filler in the tyre tread, which can lead to a weakening of the filler network and hence to further lowering of the rolling resistance.

For this purpose, numerous methods for end group modification have been developed. For example, EP0180141A1 describes the use of 4,4'-bis(dimethylamino)benzophenone or N-methylcaprolactam as functionalizing reagents. The use of ethylene oxide and N-vinylpyrrolidone is also known from EP0864606A1. A number of further possible functionalizing reagents are detailed in U.S. Pat. No. 4,417,029. Methods for introducing functional groups at the start of the polymer chains by means of functional anionic polymerization initiators are described, for example, in EP0513217A1 and EP0675140A1 (initiators with a protected hydroxyl group), US20080308204A1 (thioether-containing initiators) and in U.S. Pat. No. 5,792,820, EP0590490A1 and EP0594107A1 (alkali metal amides of secondary amines as polymerization initiators).

The carboxyl group, as a strongly polar, bidentate ligand, can interact particularly well with the surface of the silica filler in the rubber mixture. Methods for introducing carboxyl groups along the polymer chain of diene rubbers prepared in solution are known and are described, for example, in DE2653144A1, EP1000971A1, EP1050545A1, WO2009034001A1. These methods have several disadvantages, for example that long reaction times are required, that the functionalizing reagents are converted only incompletely, and that an alteration of the polymer chains occurs as a result of side reactions such as branching. Moreover, these methods do not enable particularly effective functionalization of the ends of the polymer chain.

The introduction of carboxyl groups at the chain ends of diene rubbers has likewise been described, for example in U.S. Pat. No. 3,242,129, by reaction of the anionic ends of the polymer chain with $CO_2$. This method has the disadvantage that the polymer solution has to be contacted with gaseous $CO_2$, which is found to be difficult because of the high viscosity and the resultant poor mixing. In addition, coupling reactions which are difficult to control occur as a result of reaction of more than one end of the polymer chain at the carbon atom of the $CO_2$. This coupling can be avoided by sequential reaction of the carbanionic ends of the polymer chain first with ethylene oxide or propylene oxide, followed by reaction of the ends of the polymer chain which are now alkoxidic with a cyclic anhydride (U.S. Pat. No. 4,465,809). Here too, however, there is the disadvantage that gaseous and additionally very toxic ethylene oxide or propylene oxide has to be introduced into the high-viscosity rubber solution. Furthermore, reaction of the alkoxidic chain ends with the cyclic anhydride forms hydrolysis-prone ester bonds which can be cleaved in the course of workup and in the course of later use.

Especially silanes and cyclosiloxanes having a total of at least two halogen and/or alkoxy and/or aryloxy substituents on silicon are of good suitability for end group functionalization of diene rubbers, since one of said substituents on the silicon atom can be readily exchanged in a rapid substitution reaction for an anionic diene end of the polymer chain and the further aforementioned substituent(s) on Si is/are available as a functional group which, optionally after hydrolysis, can interact with the filler of the tyre tread mixture. Examples of silanes of this kind can be found in U.S. Pat. No. 3,244,664, U.S. Pat. No. 4,185,042, EP0778311A1 and US20050203251A1.

These silanes generally have functional groups which are bonded directly to the silicon atom or bonded to Si via a spacer and can interact with the surface of the silica filler in the rubber mixture. These functional groups are generally alkoxy groups or halogens directly on Si, and tertiary amino substituents bonded to Si via a spacer. Disadvantages of these silanes are the possible reaction of a plurality of anionic ends of the polymer chain per silane molecule, elimination of troublesome components and coupling to form Si—O—Si bonds in the course of workup and storage. The introduction of carboxyl groups by means of these silanes has not been described.

WO2012/065908A1 describes 1-oxa-2-silacycloalkanes as functionalizing reagents for introduction of hydroxyl end groups in diene polymers. These 1-oxa-2-silacycloalkanes do not have the disadvantages of the silanes described in the above paragraph, such as reaction of a plurality of anionic ends of the polymer chain per silane molecule, elimination of troublesome components and coupling to form Si—O—Si bonds in the course of workup and storage. However, these functionalizing reagents also do not enable the introduction of carboxyl groups at the ends of the polymer chain.

The problem addressed was therefore that of providing carboxyl-terminated polymers which do not have the disadvantages of the prior art and more particularly enable utilization of the good reactivity of silanes having anionic ends of the polymer chain.

SUMMARY

This problem is solved through the proposal of end group-functionalized polymers having particular silane containing carboxyl groups at the end of the chain.

BRIEF DESCRIPTION OF THE DRAWINGS

FIG. 1 shows extrusion profiles of comparative and inventive compositions 3a-3e and 7a-7e.

DESCRIPTION OF THE EMBODIMENTS

End group-functionalized polymers, according to an embodiment, have, at the end of the polymer chain, a silane-containing carboxyl group of the formula (I)

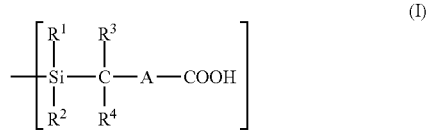

where
R$^1$, R$^2$ are the same or different and are each an H, alkyl, alkoxy, cycloalkyl, cycloalkoxy, aryl, aryloxy, alkaryl, alkaryloxy, aralkyl or aralkoxy radical which may contain one or more heteroatoms, preferably O, N, S or Si,
R$^3$, R$^4$ are the same or different and are each an H, alkyl, cycloalkyl, aryl, alkaryl or aralkyl radical which may contain one or more heteroatoms, preferably O, N, S or Si,
A is a divalent organic radical which, as well as C and H, may contain one or more heteroatoms, preferably O, N, S or Si.

Preferably, the inventive end group-functionalized polymers may be in the form of carboxylates having end groups of the formula (II):

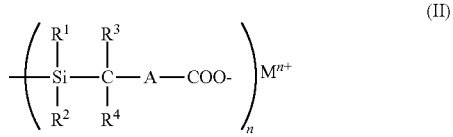

where
R$^1$, R$^2$ are the same or different and are each an H, alkyl, alkoxy, cycloalkyl, cycloalkoxy, aryl, aryloxy, alkaryl, alkaryloxy, aralkyl or aralkoxy radical which may contain one or more heteroatoms, preferably O, N, S or Si,
R$^3$, R$^4$ are the same or different and are each an H, alkyl, cycloalkyl, aryl, alkaryl or aralkyl radical which may contain one or more heteroatoms, preferably O, N, S or Si,
A is a divalent organic radical which, as well as C and H, may contain one or more heteroatoms, preferably O, N, S or Si,
n is an integer from 1 to 4,
M is a metal or semimetal of valency 1 to 4, preferably Li, Na, K, Mg, Ca, Zn, Fe, Co, Ni, Al, Nd, Ti, Sn, Si, Zr, V, Mo, W.

Preferred polymers for preparation of the Inventive end group-functionalized polymers are diene polymers, and diene copolymers obtainable by copolymerization of dienes with vinylaromatic monomers.

Preferred dienes are 1,3-butadiene, isoprene, 1,3-pentadiene, 2,3-dimethylbutadiene, 1-phenyl-1,3-butadiene and/or 1,3-hexadiene. Particular preference is given to using 1,3-butadiene and/or isoprene.

The vinylaromatic comonomers may, for example, be styrene, o-, m- and/or p-methylstyrene, p-tert-butylstyrene, α-methylstyrene, vinylnaphthalene, divinylbenzene, trivinylbenzene and/or divinylnaphthalene. Particular preference is given to using styrene.

These polymers are preferably prepared by anionic solution polymerization or by polymerization by means of coordination catalysts. In this context, coordination catalysts are understood to mean Ziegler-Natta catalysts or monometallic catalyst systems. Preferred coordination catalysts are those based on Ni, Co, Ti, Zr, Nd, V, Cr, Mo, W or Fe.

Initiators for anionic solution polymerization are those based on alkali metals or alkaline earth metals, for example methyllithium, ethyllithium, isopropyllithium, n-butyllithium, seobutyllithium, pentyllithium, n-hexyllithium, cyclohexyllithium, octyllithium, decyllithium, 2-(6-lithio-n-hexoxy)tetrahydropyran, 3-(tert-butyldimethylsiloxy)-1-propyllithium, phenyllithium, 4-butylphenyllithium, 1-naphthyllithlum, p-tolyllithlum and allyllithium compounds derived from tertiary N-allylamines, such as [1-(dimethylamino)-2-propenyl]lithium, [1-[bis(phenylmethyl)amino]-2-propenyl]lithium, [1-(diphenylamino)-2-propenyl]lithium, [1-(1-pyrrolidinyl)-2-propenyl]lithium, lithium amides of secondary amines, such as lithium pyrrolidide, lithium piperidide, lithium hexamethyleneimide, lithium 1-methylimidazolidide, lithium 1-methylpiperazide, lithium morpholide, lithium dicyclohexylamide, lithium dibenzylamide, lithium diphenylamide. These allyllithium compounds and these lithium amides can also be prepared in situ by reaction of an organolithium compound with the respective tertiary N-allylamines or with the respective secondary amines. In addition, it is also possible to use di- and polyfunctional organolithium compounds, for example 1,4-dilithiobutane, dilithium piperazide. Preference is given to using n-butyllithium and sec-butyllithium.

In addition, it is possible to use the known randomizers and control agents for the microstructure of the polymer, for example diethyl ether, di-n-propyl ether, diisopropyl ether, di-n-butyl ether, ethylene glycol dimethyl ether, ethylene glycol diethyl ether, ethylene glycol di-n-butyl ether, ethylene glycol di-tert-butyl ether, diethylene glycol dimethyl ether, diethylene glycol diethyl ether, diethylene glycol di-n-butyl ether, diethylene glycol di-ter-butyl ether, 2-(2-ethoxyethoxy)-2-methylpropane, triethylene glycol dimethyl ether, tetrahydrofuran, ethyl tetrahydrofurfuryl ether, hexyl tetrahydrofurfuryl ether, 2,2-bis(2-tetrahydrofuryl) propane, dioxane, trimethylamine, triethylamine, N,N,N',N'-tetramethylethylenediamine, N-methylmorpholine, N-ethylmorpholine, 1,2-dipiperidinoethane, 1,2- dipyrrolidinoethane, 1,2-dimorpholinoethane and potassium and sodium salts of alcohols, phenols, carboxylic acids, sulphonic acids.

Such solution polymerizations are known and are described, for example, in I. Franta, Elastomers and Rubber Compounding Materials; Elsevier 1989, pages 113-131, in Houben-Weyl, Methoden der Organischen Chemie [Methods of Organic Chemistry], Thieme Verlag, Stuttgart, 1961, volume XIV/1 pages 645 to 673 or in volume E 20 (1987), pages 114 to 134 and pages 134 to 153, and in Comprehensive Polymer Science, Vol. 4, Part II (Pergamon Press Ltd., Oxford 1989), pages 53-108.

The preparation of the preferred diene homopolymers and diene copolymers preferably takes place in a solvent. The solvents used for the polymerization are preferably inert aprotic solvents, for example paraffinic hydrocarbons such as isomeric butanes, pentanes, hexanes, heptanes, octanes, decanes, cyclopentane, methylcyclopentane, cyclohexane, methylcyclohexane, ethylcyclohexane or 1,4-dimethylcyclohexane, or alkenes such as 1-butene, or aromatic hydrocarbons such as benzene, toluene, ethylbenzene, xylene, diethylbenzene or propylbenzene. These solvents can be used individually or in combination. Preference is given to cyclohexane, methylcyclopentane and n-hexane. Blending with polar solvents is likewise possible.

The amount of solvent in the process according to the invention is typically in the range from 100 to 1000 g, preferably in the range from 200 to 700 g, based on 100 g of the total amount of monomer used. However, it is also possible to polymerize the monomers used in the absence of solvents.

The polymerization can be performed in such a way that the monomers and the solvent are initially charged and then the polymerization is started by adding the initiator or catalyst. Polymerization in a feed process is also possible, in which the polymerization reactor is filled by addition of monomers and solvent, the initiator or catalyst being initially charged or added with the monomers and the solvent. Variations such as initial charging of the solvent in the reactor, addition of the initiator or catalyst and then addition of the monomers, are possible. In addition, the polymerization can be operated in a continuous mode. Further addition of monomer and solvent during or at the end of the polymerization is possible in all cases.

The polymerization time may vary within wide limits from a few minutes to a few hours. Typically, the polymerization is performed within a period of 10 minutes up to 8 hours, preferably 20 minutes to 4 hours. It can be performed either at standard pressure or at elevated pressure (from 1 to 10 bar).

It has been found that, surprisingly, the use of one or more silalactones as functionalizing reagents can produce carboxyl-terminated polymers which do not have the disadvantages of the prior art.

The silalactones are compounds of the formula (III)

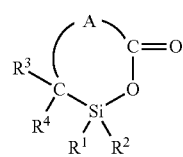

(III)

where
$R^1$, $R^2$ are the same or different and are each an H, alkyl, alkoxy, cycloalkyl, cycloalkoxy, aryl, aryloxy, alkaryl, alkaryloxy, aralkyl or aralkoxy radical which may contain one or more heteroatoms, preferably O, N, S or Si, $R^3$, $R^4$ are the same or different and are each an H, alkyl, cycloalkyl, aryl, alkaryl or aralkyl radical which may contain one or more heteroatoms, preferably O, N, S or Si, A is a divalent organic radical which, as well as C and H, may contain one or more heteroatoms, preferably O, N, S or Si, where preferably $R^1$, $R^2$ are the same or different and are each an H, ($C_1$-$C_{24}$)-alkyl, ($C_1$-$C_2$)-alkoxy, ($C_3$-$C_{24}$)-cycloalkyl, ($C_3$-$C_{24}$)-cycloalkoxy, ($C_6$-$C_{24}$)-aryl, ($C_6$-$C_{24}$)-aryloxy, ($C_6$-$C_{24}$)-alkaryl, ($C_6$-$C_{24}$)-alkaryloxy, ($C_6$-$C_{24}$)-aralkyl or ($C_6$-$C_{24}$)-aralkoxy radical which may contain one or more heteroatoms, preferably O, N, S or Si, and $R^3$, $R^4$ are the same or different and are each an H, ($C_1$-$C_{24}$)-alkyl, ($C_3$-$C_{24}$)-cycloalkyl, ($C_6$-$C_{24}$)-aryl, ($C_6$-$C_{24}$)-alkaryl or ($C_6$-$C_{24}$)-aralkyl radical which may contain one or more heteroatoms, preferably O, N, S or Si.

Examples of compounds of the formula (III) are:
2,2-dimethyl-1-oxa-2-silacyclohexan-6-one (1), 2,2,4-trimethyl-1-oxa-2-silacyclohexan-6-one (2), 2,2,5-trimethyl-1-oxa-2-silacyclohexan-6-one (3), 2,2,4,5-tetramethyl-1-oxa-2-silacyclohexan-6-one (4), 2,2-diethyl-1-oxa-2-silacyclohexan-6-one (5), 2,2-diethoxy-1-oxa-2-silacyclohexan-6-one (6), 2,2-dimethyl-1,4-dioxa-2-silacyclohexan-6-one (7), 2,2,5-trimethyl-1,4-dioxa-2-silacyclohexan-6-one (8), 2,2,3,3-tetramethyl-1,4-dioxa-2-silacyclohexan-6-one (9), 2,2-dimethyl-1-oxa-4-thia-2-silacyclohexan-6-one (10), 2,2-dethyl-1-oxa-4-thia-2-silacyclohexan-6-one (11), 2,2-diphenyl-oxa-4-thia-2-silacyclohexan-6-one (12), 2-methyl-2-ethenyl-1-oxa-4-thia-2-silacyclohexan-6-one (13), 2,2,5-trimethyl-1-oxa-4-thia-2-silacyclohexan-6-one (14), 2,2-dimethyl-1-oxa-4-aza-2-silacyclohexan-6-one (15), 2,2,4-trimethyl-1-oxa-4-aza-2-silacyclohexan-6-one (16), 2,4-dimethyl-2-phenyl-1-oxa-4-aza-2-silacyclohexan-6-one (17), 2,2-dimethyl-4-trimethylsilyl-1-oxa-4-aza-2-silacyclohexan-6-one (18), 2,2-diethoxy-4-methyl-1-oxa-4-aza-2-silacyclohexan-6-one (19), 2,2,4,4-tetramethyl-1-oxa-2,4-disilacyclohexan-6-one (20), 3,4-dihydro-3,3-dimethyl-1H-2,3-benzoxasilin-1-one (21), 2,2-dimethyl-1-oxa-2-silacyclopentan-5-one (22), 2,2,3-methyl-1-oxa-2-silacyclopentan-5-one (23), 2,2-dimethyl-4-phenyl-1-oxa-2-silacyclopentan-5-one (24), 2,2-di(tert-butyl)-1-oxa-2-silacyclopentan-5-one (25), 2-methyl-2-(2-propen-1-yl)-1-oxa-2-silacyclopentan-5-one (26), 1,1-dimethyl-2,1-benzoxasilol-3(1H)-one (27), 2,2-dimethyl-1-oxa-2-silacycloheptan-7-one (28).

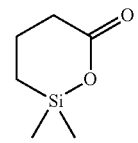

(1)

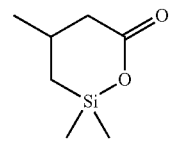

(2)

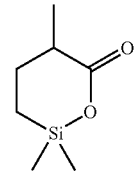

(3)

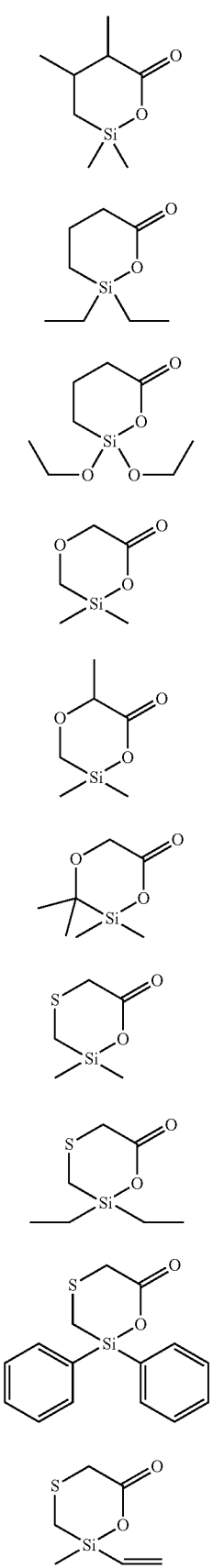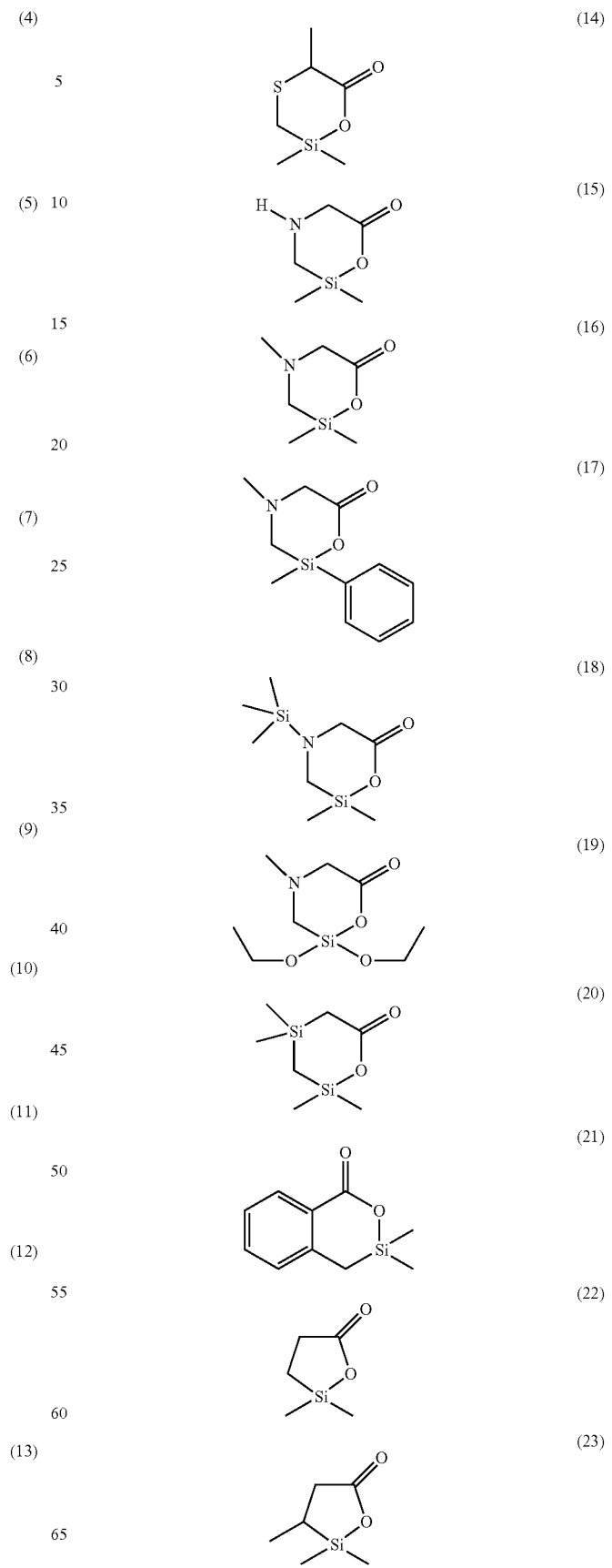

-continued

(24)
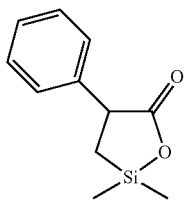

(25)
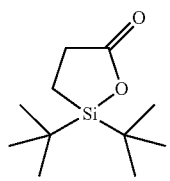

(26)
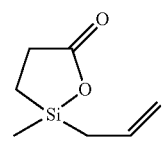

(27)
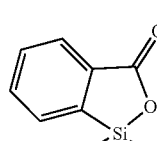

(28)
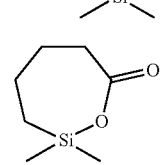

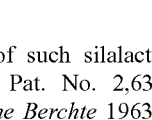

The syntheses of such silalactones are described, for example, in U.S. Pat. No. 2,635,109; M. Wieber, M. Schmidt, *Chemische Berchte* 1963, 96 (10), 2822-5; J. M. Wolcott, F. K. Cartledge, *Journal of Organic Chemistry* 1974, 39 (16), 2420-4; M. P. Sibi, J. W. Christensen, *Tetrahedron Letters* 1995, 36 (35), 6213-6; T. Linker, M. Maurer, F. Reblen, *Tetrahedron Letters* 1996, 37 (46), 8363-6; M. Shindo et al., *Angewandte Chemie, International Edition* 2004, 43 (1), 104-6.

It has been found that the inventive end group-functionalized polymers can be prepared by reaction of reactive ends of the polymer chains with silalactones and optional subsequent protonation of the carboxylate end group produced to give the carboxyl end group.

Thus, the Invention also provides for the use of silalactones as functionalizing reagents for preparation of the inventive end group-functionalized polymers having end groups of the formula (I) or (II).

When polymers having very reactive nucleophilic ends of the polymer chains are reacted with silalactones of the formula (III), the polymer chains cannot only be attached on the silicon atom of the functionalizing reagent; in addition, attachment may additionally occur on the carbonyl carbon atom. This leads to linear coupling of the polymer chains which do not have any functional end groups of formula (I) or (II). These coupling products are referred to in the context of the application as "dimers". One example of a linear coupling of the polymer chains is shown in Scheme 1, and further dimers may also form depending on the ring opening of the silalactone. A feature common to all the dimers that form is that they have one or more structural elements derived from silalactones of the formula (III), preferably a structural element of the formula (IV)

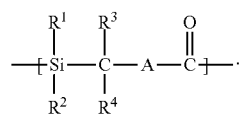 (IV)

On preparation of the polymers, addition of the functionalizing reagent gives rise to a polymer mixture comprising end group-functionalized polymer and dimer containing one or more structural elements derived from silalactones of the formula (III). Polymers having very reactive nucleophilic ends of the polymer chains are, for example, diene homopolymers and diene copolymers, which are prepared by means of anionic polymerization or with coordination catalysts.

Scheme 1

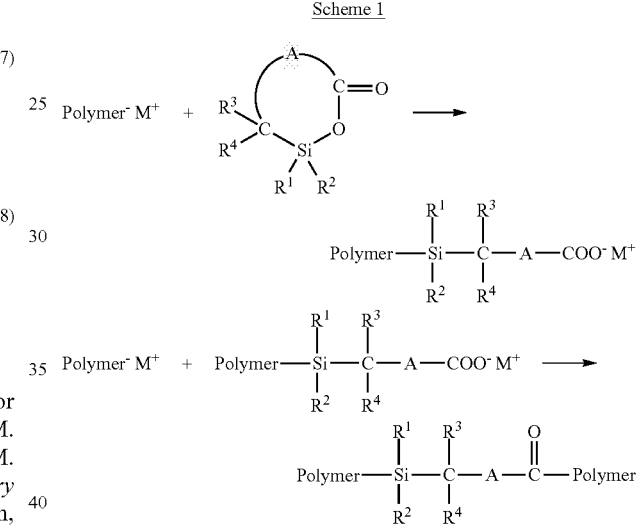

Polymer⁻: polymer chain having a reactive chain end
M⁺: Counterion, e.g. Li⁺

The dimer content in the polymer mixture is typically in the range from 10 to 90% by weight, based on the total content of polymer. Coupling reactions of this kind may be desirable in some cases, in order to increase the polydispersity and in this way to influence rheological properties of the polymer mixtures, such as Mooney viscosity, cold flow and processing characteristics.

The inventive polymer mixtures preferably have mean molar masses (number-average, $M_n$) of 10 000 to 2 000 000 g/mol, preferably of 100 000 to 1 000 000 g/mol, and glass transition temperatures of −110° C. to +20° C., preferably of −110° C. to 0° C., and Mooney viscosities [ML 1+4 (100° C.)] of 10 to 200, preferably of 30 to 150, Mooney units.

The invention further provides a process for preparing the inventive end group-functionalized polymers, in which one or more compounds of the formula (II) are added, as a pure substance, solution or suspension, to give polymers having reactive ends of the polymer chains. The addition preferably follows conclusion of the polymerization, but may also precede complete monomer conversion. The reaction of silalactones of the formula (III) with polymers having reactive ends of the polymer chains is effected at the temperatures customarily used for the polymerization. The reaction times for the reaction of silalactones of the formula (III) with the reactive ends of the polymer chains may be between a few minutes and several hours. The amount of these compounds can be selected such that all the reactive ends of the polymer chains react with silalactones of the formula (III), wherein the compounds are in excess of the reactive ends, or both are in stoichiometric amounts. Alternatively, it is possible to use a deficiency of these compounds. The amounts of the compounds of the formula (III) used may cover a wide range. The preferred amounts are within a range from 0.005 to 2% by weight, more preferably within a range from 0.01 to 1% by weight, based on the amount of polymer.

In addition to silalactones of the formula (III), it is also possible to use the coupling reagents typical of anionic diene polymerization for reaction with the reactive ends of the polymer chains. Examples of such coupling reagents are silicon tetrachloride, methyltrichlorosilane, dimethyldichlorosilane, tin tetrachloride, dibutyltin dichloride, tetraalkoxysilanes, ethylene glycol diglycidyl ether, 1,2,4-tris(chloromethyl)benzene. Such coupling reagents can be added prior to, together with or after the silalactones of the formula (III).

On completion of addition of silalactones of the formula (III) and optionally of coupling reagents, before or during the workup of the inventive silane-containing, carboxylate-terminated polymers, preference is given to adding the customary ageing stabilizers, such as sterically hindered phenols, aromatic amines, phosphites, thioethers. In addition, it is possible to add the customary extender oils used for diene rubbers, such as DAE (Distillate Aromatic Extract), TDAE (Treated Distillate Aromatic Extract), MES (Mild Extraction Solvates), RAE (Residual Aromatic Extract), TRAE (Treated Residual Aromatic Extract), naphthenic and heavy naphthenic oils. It is also possible to add fillers, such as carbon black and silica, rubbers and rubber auxiliaries.

The solvent can be removed from the polymerization process by the customary methods, such as distillation, stripping with steam or application of reduced pressure, optionally at elevated temperature.

The invention further provides for the use of the inventive end group-functionalized polymers for production of vulcanizable rubber compositions.

These vulcanizable rubber compositions preferably comprise further rubbers, fillers, rubber chemicals, processing aids and extender oils.

Additional rubbers are, for example, natural rubber and synthetic rubbers. If present, the amount thereof is preferably within the range from 0.5 to 95% by weight, preferably within the range from 10 to 80% by weight, based on the total amount of polymer in the mixture. The amount of rubbers additionally added is again guided by the respective end use of the Inventive mixtures.

Examples of synthetic rubbers of this kind are BR (polybutadiene), acrylic acid-alkyl ester copolymers, IR (polyisoprene), E-SBR (styrene-butadiene copolymers prepared by emulsion polymerization), S-SBR (styrene-butadiene copolymers prepared by solution polymerization), IIR (isobutylene-isoprene copolymers), NBR (butadiene-acrylonitrile copolymers), HNBR (partly hydrogenated or fully hydrogenated NBR rubber), EPDM (ethylene-propylene-diene terpolymers) and mixtures of these rubbers. For the production of car tyres, particularly natural rubber, E-SBR and S-SBR having a glass transition temperature above −60° C., polybutadiene rubber which has a high cis content (>90%) and has been prepared with catalysts based on Ni, Co, Ti or Nd, and polybutadiene rubber having a vinyl content of up to 80% and mixtures thereof are of interest.

Useful fillers for the inventive rubber compositions include all known fillers used in the rubber industry. These include both active and inactive fillers.

The following should be mentioned by way of example:

finely divided silicas, produced, for example, by precipitation of solutions of silicates or flame hydrolysis of silicon halides having specific surface areas of 5-1000, preferably 20-400, $m^2/g$ (BET surface area) and having primary particle sizes of 10-400 nm. The silicas may optionally also be present as mixed oxides with other metal oxides, such as oxides of Al, Mg, Ca, Ba, Zn, Zr, Ti;

synthetic silicates, such as aluminium silicate, alkaline earth metal silicates such as magnesium silicate or calcium silicate, having BET surface areas of 20-400 $m^2/g$ and primary particle diameters of 10-400 nm;

natural silicates, such as kaolin, montmorillonite and other naturally occurring silicas;

glass fibres and glass fibre products (mats, strands) or glass microspheres;

metal oxides, such as zinc oxide, calcium oxide, magnesium oxide, aluminium oxide;

metal carbonates, such as magnesium carbonate, calcium carbonate, zinc carbonate;

metal hydroxides, for example aluminium hydroxide, magnesium hydroxide;

metal sulphates, such as calcium sulphate, barium sulphate;

carbon blacks: The carbon blacks to be used here are carbon blacks produced by the lamp black, channel black, furnace black, gas black, thermal black, acetylene black or light are process and have BET surface areas of 9-200 $m^2/g$, for example SAF, ISAF-LS, ISAF-HM, ISAF-LM, ISAF-HS, CF, SCF, HAF-LS, HAF, HAF-HS, FF-HS, SPF, XCF, FEF-LS, FEF, FEF-HS, GPF-HS, GPF, APF, SRF-LS, SRF-LM, SRF-HS, SRF-HM and MT carbon blacks, or ASTM N110, N219, N220, N231, N234, N242, N294, N326, N327, N330, N332, N339, N347, N351, N356, N358, N375, N472, N539, N550, N568, N650, N660, N754, N762, N765, N774, N787 and N990 carbon blacks.

rubber gels, especially those based on BR, E-SBR and/or polychloroprene having particle sizes of 5 to 1000 nm.

The fillers used are preferably finely divided silicas and/or carbon blacks.

The fillers mentioned can be used alone or in a mixture. In a particularly preferred embodiment, the rubber compositions comprise, as filers, a mixture of light-coloured fillers, such as finely divided silicas, and carbon blacks, the mixing ratio of light-coloured fillers to carbon blacks being 0.01:1 to 50:1, preferably 0.05:1 to 20:1.

The fillers are used here in amounts in the range from 10 to 500 parts by weight based on 100 parts by weight of rubber. Preference is given to using amounts within a range from 20 to 200 parts by weight.

In a further embodiment of the invention, the rubber compositions also comprise rubber auxiliaries which, for example, Improve the processing properties of the rubber compositions, serve to crosslink the rubber compositions, improve the physical properties of the vulcanizates produced from the inventive rubber compositions for the specific end use thereof, improve the interaction between rubber and filler, or serve for attachment of the rubber to the filer.

Rubber auxiliaries are, for example, crosslinker agents, for example sulphur or sulphur-supplying compounds, and also reaction accelerators, ageing stabilizers, heat stabilizers, light stabilizers, antozonants, processing aids, plasticizers, tackifiers, blowing agents, dyes, pigments, waxes, extenders, organic acids, silanes, retardants, metal oxides, extender oils, for example DAE (Distillate Aromatic Extract), TDAE (Treated Distillate Aromatic Extract), MES (Mild Extraction Solvates), RAE (Residual Aromatic Extract), TRAE (Treated Residual Aromatic Extract), naphthenic and heavy naphthenic oils and activators.

The total amount of rubber auxiliaries is within the range from 1 to 300 parts by weight, based on 100 parts by weight of overall rubber. Preference is given to using amounts within the range from 5 to 150 parts by weight of rubber auxiliaries.

The vulcanizable rubber compositions can be produced in a one-stage or in a multistage process, preference being given to 2 to 3 mixing stages. For example, sulphur and accelerator can be added in a separate mixing stage, for example on a roller, preferred temperatures being in the range from 30 to 90° C. Preference is given to adding sulphur and accelerator in the last mixing stage.

Examples of equipment suitable for the production of the vulcanizable rubber compositions include rollers, kneaders, internal mixtures or mixing extruders.

Thus, the Invention further provides vulcanizable rubber compositions comprising end group-functionalized polymers having end groups of the formula (I) or (II).

The Inventive polymers or rubber mixtures thereof combine low cold flow, good dynamic properties and good processing characteristics.

The invention further provides for the use of the inventive vulcanizable rubber compositions for production of rubber vulcanizates, especially for the production of tyres, especially tyre treads, having particularly low rolling resistance coupled with high wet skid resistance and abrasion resistance.

The inventive vulcanizable rubber compositions are also suitable for production of mouldings, for example for the production of cable sheaths, hoses, drive belts, conveyor belts, roll covers, shoe soles, gasket rings and damping elements.

The examples which follow serve to illustrate the invention but have no limiting effect.

EXAMPLES

Example 1a: Synthesis of Unfunctionalized Styrene-Butadiene Copolymer (Comparative Example)

An inertized 20 l reactor was charged with 8.5 kg of hexane, 1185 g of 1,3-butadiene, 315 g of styrene, 8.6 mmol of 2,2-bis(2-tetrahydrofuryl)propane and 11.3 mmol of butyllithium, and the contents were heated to 60° C. Polymerization was effected while stirring at 60° C. for 25 minutes. Subsequently, 11.3 mmol of cetyl alcohol were added to cap the anionic ends of the polymer chains, the rubber solution was discharged and stabilized by addition of 3 g of Irganox® 1520 (2,4-bis(octylthiomethyl)-6-methylphenol), and the solvent was removed by stripping with steam. The rubber crumbs were dried at 65° C. under reduced pressure.

Example 1b: Synthesis of Carboxyl-Terminated Styrene-Butadiene Copolymer by Reaction with Silalactone (Inventive)

The procedure was as in Example 1a. In place of the cetyl alcohol, however, an amount of 2,2-dimethyl-1-oxa-4-thia-2-silacyclohexan-6-one equimolar to that of butyllithium was added (as a solution in toluene) and the reactor contents were then heated to 60° C. for a further 20 minutes.

Example 1c: Synthesis of Carboxyl-Terminated Styrene-Butadiene Copolymer Having a Tertiary Amino Group at the Start of the Chain by Reaction with Silalactone (Inventive)

The procedure was as in Example 1b. Prior to addition of the butyllithium, however, an amount of pyrrolidine equimolar to that of butyllithium was added.

Example 1d: Synthesis of Hydroxyl-Terminated Styrene-Butadiene Copolymer by Reaction with Caprolactone (Comparative Example)

The procedure was as in Example 1b. In place of the silalactone, however, an amount of ε-caprolactone equimolar to that of butyllithium was added.

Example 1e: Synthesis of Hydroxyl-Terminated Styrene-Butadiene Copolymer by Reaction with 1-Oxa-2-Silacycloalkane (Comparative Example)

The procedure was as in Example 1b. In place of the silalactone, however, an amount of 2,2,4-trimethyl-1-oxa-4-aza-2-silacyclohexane equimolar to that of butyllithium was added (as a solution in hexane).

The polymer properties of the styrene-butadiene copolymers from Examples 1a-e are summarized in Table 1.

Examples 2a-e: Rubber Compositions

Tyre tread rubber compositions comprising the styrene-butadiene copolymers of Examples 1a-e were produced. The constituents are listed in Table 2. The rubber compositions (apart from sulphur and accelerator) were produced in a 1.5 l kneader. The sulphur and accelerator constituents were subsequently mixed in on a roller at 40° C.

Examples 3a-e: Extrusion Profiles

To assess the processing characteristics of the rubber compositions of Examples 2a-e, a laboratory extruder at 120° C. was used to produce extrusion profiles (Garvey profiles) (Brabender PV 301 extruder (16 mm), die diameter 14.5 mm, S08 mouthpiece, screw speed 50 revolutions per minute). These Garvey profiles are shown in the appendix, Figures I/3a-e.

TABLE 1

Properties of the styrene-butadiene copolymers of Examples 1a-e

| SBR from Ex. | Functionalizing reagent | Vinyl content [a] [% by wt.] | Styrene content [a] [% by wt.] | Tg [b] [° C.] | $M_p1$ [c] [kg/mol] | $M_p2$ [c] [kg/mol] | Degree of coupling [c] [%] | ML1 + 4 [d] [MU] | Cold flow [e] [mg/min] |
|---|---|---|---|---|---|---|---|---|---|
| 1a (comparative) | — | 51.5 | 20.9 | −23 | 280 | — | 0 | 42 | 21 |
| 1b (inventive) | silalactone | 50.8 | 21.8 | −23 | 298 | 620 | 44 | 84 | 2 |
| 1c (inventive) | silalactone | 50.9 | 20.4 | −24 | 283 | 449 | 38 | 75 | 2 |
| 1d (comparative) | caprolactone | 51.8 | 22.3 | −20 | 264 | 560 | 28 | 56 | 8 |

TABLE 1-continued

Properties of the styrene-butadiene copolymers of Examples 1a-e

| SBR from Ex. | Functionalizing reagent | Vinyl content [a] [% by wt.] | Styrene content [a] [% by wt.] | Tg [b] [° C.] | $M_p1$ [c] [kg/mol] | $M_p2$ [c] [kg/mol] | Degree of coupling [c] [%] | ML1 + 4 [d] [MU] | Cold flow [e] [mg/min] |
|---|---|---|---|---|---|---|---|---|---|
| 1e (comparative) | 1-oxa-2-silacyclohexane | 50.9 | 21.5 | −23 | 256 | — | 0 | 37 | 25 |

[a] determination of vinyl and styrene contents by FTIR
[b] determination of glass transition temperature by DSC
[c] determination of peak molecular weights $M_p1$ and $M_p2$ and of degree of coupling by GPC (PS calibration)
[d] determination of Mooney viscosity at 100° C.
[e] determination of cold flow at 50° C.

TABLE 2

Constituents of the tyre tread rubber compositions (FIGURES in phr: parts by weight per 100 parts by weight of rubber)

|  | Comparative Example 2a | Inventive Example 2b | Inventive Example 2c | Comparative Example 2d | Comparative Example 2e |
|---|---|---|---|---|---|
| styrene-butadiene copolymer from Example 1a | 70 | 0 | 0 | 0 | 0 |
| styrene-butadiene copolymer from Example 1b | 0 | 70 | 0 | 0 | 0 |
| styrene-butadiene copolymer from Example 1c | 0 | 0 | 70 | 0 | 0 |
| styrene-butadiene copolymer from Example 1d | 0 | 0 | 0 | 70 | 0 |
| styrene-butadiene copolymer from Example 1e | 0 | 0 | 0 | 0 | 70 |
| high-cis polybutadiene (BUNA ™ CB 24 from Lanxess Deutschland GmbH) | 30 | 30 | 30 | 30 | 30 |
| silica (Ultrasil ® 7000) | 90 | 90 | 90 | 90 | 90 |
| carbon black (Vulcan ® J/N 375) | 7 | 7 | 7 | 7 | 7 |
| TDAE oil (Vivatec 500) | 36.3 | 36.3 | 36.3 | 36.3 | 36.3 |
| processing aid (Aflux 37) | 3 | 3 | 3 | 3 | 3 |
| stearic acid (Edenor C 18 98-100) | 1 | 1 | 1 | 1 | 1 |
| ageing stabilizer (Vulkanox ® 4020/LG from Lanxess Deutschland GmbH) | 2 | 2 | 2 | 2 | 2 |
| ageing stabilizer (Vulkanox ® HS/LG from Lanxess Deutschland GmbH) | 2 | 2 | 2 | 2 | 2 |
| zinc oxide (Rotsiegel zinc white) | 3 | 3 | 3 | 3 | 3 |
| wax (Antilux 654) | 2 | 2 | 2 | 2 | 2 |
| silane (Si 69 ® from Evonik) | 7.2 | 7.2 | 7.2 | 7.2 | 7.2 |
| diphenylguanidine (Rhenogran DPG-80) | 2.75 | 2.75 | 2.75 | 2.75 | 2.75 |
| sulphenamide (Vulkacit ® NZ/EGC from Lanxess Deutschland GmbH) | 1.6 | 1.6 | 1.6 | 1.6 | 1.6 |
| sulphur (Chancel 90/95 ground sulphur) | 1.6 | 1.6 | 1.6 | 1.6 | 1.6 |
| sulphonamide (Vulkalent ® E/C) | 0.2 | 0.2 | 0.2 | 0.2 | 0.2 |

Examples 4a-e: Vulcanizate Properties

The tyre tread rubber compositions of Examples 2a-e according to Table 2 were vulcanized at 160° C. for 20 minutes. The properties of the corresponding vulcanizates are listed in Table 3 as Examples 4a-e. The vulcanizate properties of the vulcanized sample from Comparative Example 4a comprising the unfunctionalized styrene-butadiene copolymer are given the index 100. All values greater than 100 in Table 3 mean a corresponding percentage improvement in the respective test property.

TABLE 3

| | Vulcanizate properties | | | | |
|---|---|---|---|---|---|
| | Comparative Example 4a | Inventive Example 4b | Inventive Example 4c | Comparative Example 4d | Comparative Example 4e |
| Styrene-butadiene copolymer in the vulcanizate: | | | | | |
| styrene-butadiene copolymer from Example 1a | X | | | | |
| styrene-butadiene copolymer from Example 1b | | X | | | |
| styrene-butadiene copolymer from Example 1c | | | X | | |
| styrene-butadiene copolymer from Example 1d | | | | X | |
| styrene-butadiene copolymer from Example 1e | | | | | X |
| Vulcanizate properties: | | | | | |
| tan δ at 0° C. (dynamic damping at 10 Hz) | 100 | 116 | 118 | 109 | 115 |
| tan δ at 60° C. (dynamic damping at 10 Hz) | 100 | 113 | 131 | 109 | 117 |
| tan δ maximum (MTS amplitude sweep at 1 Hz, 60° C.) | 100 | 115 | 122 | 110 | 117 |

TABLE 3-continued

| Vulcanizate properties | Comparative Example 4a | Inventive Example 4b | Inventive Example 4c | Comparative Example 4d | Comparative Example 4e |
|---|---|---|---|---|---|
| ΔG* (G*@0.5%-G*@15% from MTS amplitude sweep) [MPa] | 100 | 134 | 167 | 116 | 189 |
| Resilience at 60° C. [%] | 100 | 110 | 109 | 113 | 114 |
| Abrasion (DIN 53516) [mm$^3$] | 100 | 121 | 116 | 114 | 113 |

The cold flow value of rubbers is a measure of the flow characteristics of the rubber during storage. Garvey profiles of unvulcanized rubber mixtures serve for assessment of the processing characteristics of rubber mixtures. In the case of vulcanized tyre tread mixtures, the resilience at 60° C., the dynamic damping tan δ at 60° C., the tan δ maximum in the amplitude sweep and the module difference ΔG* between low and high strain in the amplitude sweep are indicators of rolling resistance in the tyre. The dynamic damping tan δ at 0° C. is an indicator of the wet skid resistance of the tyre. The DIN abrasion is an indicator of the abrasion resistance of the tyre tread.

As illustrated by Figures I/3a-e, al tyre tread rubber compositions 2a-e show good processing characteristics (smooth Garvey profiles 3a-e). As apparent from Table 1, however, only the inventive polymers of Examples 1b and 1c feature very low cold flow values. It is apparent from Table 3 that the vulcanized tyre tread mixtures 4b and 3c, comprising the inventive polymers 1b and 1c, and the vulcanized tyre tread mixture 4e, comprising the comparative polymer 1e, additionally have particularly advantageous test values for rolling resistance, wet skid resistance and abrasion resistance.

Example 5a: Synthesis of Unfunctionalized Styrene-Butadiene Copolymer (Comparative Example)

An inertized 20 l reactor was charged with 8.5 kg of hexane, 1185 g of 1,3-butadiene, 315 g of styrene, 8.6 mmol of 2,2-bis(2-tetrahydrofuryl)propane and 9.5 mmol of butyllithium, and the contents were heated to 60° C. Polymerization was effected while stirring at 60° C. for 25 minutes. Subsequently, 9.5 mmol of cetyl alcohol were added to cap the anionic ends of the polymer chains, the rubber solution was discharged and stabilized by addition of 3 g of Irganox® 1520 (2,4-bis(octylthiomethyl)-6-methylphenol), and the solvent was removed by stripping with steam. The rubber crumbs were dried at 65° C. under reduced pressure.

Example 5b: Synthesis of Carboxyl-Terminated Styrene-Butadiene Copolymer by Reaction with Silalactone (Inventive)

The procedure was as in Example 1b.

Example 5c: Synthesis of Hydroxyl-Terminated Styrene-Butadiene Copolymer by Reaction with Caprolactone (Comparative Example)

The procedure was as in Example 1d. However, 10 mmol of butyllithium and an equimolar amount of ε-caprolactone were used.

Example 5d: Syntheses of Hydroxyl-Terminated Styrene-Butadiene Copolymer by Reaction with 1-oxa-2-silacycloalkane (Comparative Example)

The procedure was as in Example 1e. However, 9.5 mmol of butyllithium and an equimolar amount of 2,2,4-trimethyl-1-oxa-4-aza-2-silacyclohexane were used.

Example 5e: Synthesis of Silanol-Terminated Styrene-Butadiene Copolymer by Reaction with Hexamethylcyclotrisiloxane (Comparative Example)

The procedure was as in Example 5d. In place of the 2,2,4-trimethyl-1-oxa-4-aza-2-silacyclohexane, however, an amount of hexamethylcyclotrisiloxane equimolar to that of butyllithium was added.

The polymer properties of the styrene-butadiene copolymers from Examples 5a-e are summarized in Table 4.

Examples 6a-e: Rubber Compositions

Tyre tread rubber compositions comprising the styrene-butadiene copolymers of Examples 5a-e were produced. The constituents are listed in Table 5. The rubber compositions (apart from sulphur and crosslinker) were produced in a 1.5 l kneader. The sulphur and accelerator constituents were subsequently mixed in on a roller at 40° C.

Examples 7a-e: Extrusion Profiles

To assess the processing characteristics of the rubber compositions of Examples 6a-e, as described above, extrusion profiles (Garvey profiles) were produced by means of a laboratory extruder at 120° C. These Garvey profiles are shown in the appendix, Figures I/7a-e.

TABLE 4

| Properties of the styrene-butadiene copolymers of Examples 5a-d | | | | | | | | | |
|---|---|---|---|---|---|---|---|---|---|
| SSBR from Ex. | Functionalizing reagent | Vinyl content [% by wt.] [a] | Styrene content [% by wt.] [a] | Tg [° C.] [b] | $M_p1$ [kg/mol] [c] | $M_p2$ [kg/mol] [c] | Degree of coupling [%] [e] | ML1 + 4 [MU] [d] | Cold flow [mg/min] [e] |
| 5a (comparative) | — | 50.1 | 20.0 | −26 | 397 | — | 0 | 78 | 9 |
| 5b (inventive) | silalactone | 50.7 | 21.2 | −22 | 260 | 534 | 61 | 88 | 0 |
| 5c (comparative) | caprolactone | 50.4 | 21.9 | −22 | 366 | 791 | 27 | 87 | 2 |

TABLE 4-continued

Properties of the styrene-butadiene copolymers of Examples 5a-d

| SSBR from Ex. | Functionalizing reagent | Vinyl content [a] [% by wt.] | Styrene content [a] [% by wt.] | Tg [b] [° C.] | $M_p1$ [c] [kg/mol] | $M_p2$ [c] [kg/mol] | Degree of coupling [c] [%] | ML1 + 4 [d] [MU] | Cold flow [e] [mg/min] |
|---|---|---|---|---|---|---|---|---|---|
| 5d (comparative) | 1-oxa-2-silacyclohexane | 50.1 | 20.8 | −25 | 364 | — | 0 | 81 | 6 |
| 5e (comparative) | hexamethylcyclo-trisiloxane | 51.6 | 21.7 | −21 | 368 | — | 0 | 80 | 6 |

[a] determination of vinyl and styrene contents by FTIR
[b] determination of glass transition temperature by DSC
[c] determination of peak minder weights $M_p1$ and $M_p2$ and of degree of coupling by GPC (PS calibration)
[d] determination of Mooney viscosity at 100° C.
[e] determination of cold flow at 50° C.

TABLE 5

Constituents of the tyre tread rubber compositions (FIGURES in phr: parts by weight per 100 parts by weight of rubber)

| | Comparative Example 6a | Inventive Example 6b | Comparative Example 6c | Comparative Example 6d | Comparative Example 6e |
|---|---|---|---|---|---|
| styrene-butadiene copolymer from Example 5a | 70 | 0 | 0 | 0 | 0 |
| styrene-butadiene copolymer from Example 5b | 0 | 70 | 0 | 0 | 0 |
| styrene-butadiene copolymer from Example 5c | 0 | 0 | 70 | 0 | 0 |
| styrene-butadiene copolymer from Example 5d | 0 | 0 | 0 | 70 | 0 |
| styrene-butadiene copolymer from Example 5e | 0 | 0 | 0 | 0 | 70 |
| high-cis polybutadiene (BUNA ™ CB 24 from Lanxess Deutschland GmbH) | 30 | 30 | 30 | 30 | 30 |
| silica (Ultrasil ® 7000) | 90 | 90 | 90 | 90 | 90 |
| carbon black (Vulcan ® J/N 375) | 7 | 7 | 7 | 7 | 7 |
| TDAE oil (Vivatec 500) | 36.3 | 36.3 | 36.3 | 36.3 | 36.3 |
| processing aid (Aflux 37) | 3 | 3 | 3 | 3 | 3 |
| stearic acid (Edenor C 18 98-100) | 1 | 1 | 1 | 1 | 1 |
| ageing stabilizer (Vulkanox ® 4020/LG from Lanxess Deutschland GmbH) | 2 | 2 | 2 | 2 | 2 |
| ageing stabilizer (Vulkanox ® HS/LG from Lanxess Deutschland GmbH) | 2 | 2 | 2 | 2 | 2 |
| zinc oxide (Rotsiegel zinc white) | 3 | 3 | 3 | 3 | 3 |
| wax (Antilux 654) | 2 | 2 | 2 | 2 | 2 |
| silane (Si 69 ® from Evonik) | 7.2 | 72 | 7.2 | 7.2 | 7.2 |
| diphenylguanidine (Rhenogran DPG-80) | 2.75 | 2.75 | 2.75 | 2.75 | 2.75 |
| sulphenamide (Vulkacit ® NZ/EGC from Lanxess Deutschland GmbH) | 1.6 | 1.6 | 1.6 | 1.6 | 1.6 |
| sulphur (Chancel 90/95 ground sulphur) | 1.6 | 1.6 | 1.6 | 1.6 | 1.6 |
| sulphonamide (Vulkalent ® E/C) | 0.2 | 0.2 | 0.2 | 0.2 | 0.2 |

Examples 8a-d: Vulcanizate Properties

The tyre tread rubber compositions of Examples 6a-e according to Table 5 were vulcanized at 160° C. for 20 minutes. The properties of the corresponding vulcanizates are listed in Table 6 as Examples 8a-e. The vulcanizate properties of the vulcanized sample from Comparative Example ea comprising the unfunctionalized styrene-butadiene copolymer are given the index 100. All values greater than 100 in Table 6 mean a corresponding percentage improvement in the respective test property.

TABLE 6

Vulcanizate properties

| | Comparative Example 8a | Inventive Example 8b | Comparative Example 8c | Comparative Example 8d | Comparative Example 8e |
|---|---|---|---|---|---|
| Styrene-butadiene copolymer in the vulcanizate: | | | | | |
| styrene-butadiene copolymer from Example 5a | X | | | | |
| styrene-butadiene copolymer from Example 5b | | X | | | |
| styrene-butadiene copolymer from Example 5c | | | X | | |
| styrene-butadiene copolymer from Example 5d | | | | X | |
| styrene-butadiene copolymer from Example 5e | | | | | X |

TABLE 6-continued

Vulcanizate properties

|  | Comparative Example 8a | Inventive Example 8b | Comparative Example 8c | Comparative Example 8d | Comparative Example 8e |
|---|---|---|---|---|---|
| Vulcanizate properties: | | | | | |
| tan δ at 0° C. (dynamic damping at 10 Hz) | 100 | 120 | 109 | 102 | 111 |
| tan δ at 60° C. (dynamic damping at 10 Hz) | 100 | 113 | 115 | 122 | 112 |
| tan δ maximum (MTS amplitude sweep at 1 Hz, 60° C.) | 100 | 108 | 100 | 110 | 112 |
| ΔG* (G*@0.5%-G*@15% from MTS amplitude sweep) [MPa] | 100 | 125 | 107 | 150 | 136 |
| Resilience at 60° C. [%] | 100 | 107 | 110 | 109 | 105 |
| Abrasion (DIN 53516) [mm³] | 100 | 117 | 103 | 120 | 110 |

As apparent from Table 4, all the polymers of Examples 5a-e feature low cold flow values. As illustrated by Figures I/7a-e, the tyre tread rubber compositions 6a, 6b and 6c, comprising the polymers of Examples 5a (comparative), 5b (inventive) and 5c (comparative) show good processing characteristics (smooth Garvey profiles 7a, 7b, 7c). The tyre tread rubber compositions 6d and 6e, comprising the comparative polymers 5d and 5e, in contrast, have poorer processing characteristics (rough Garvey profiles 7d, 7e). It is apparent from Table 6 that the vulcanized tyre tread mixture 8b, comprising the inventive polymer 5b, and the vulcanized tyre tread mixtures 8d and 8e, comprising the comparative polymers 5d and 5e, have particularly advantageous test values for rolling resistance, wet skid resistance and abrasion resistance.

The examples make it clear that only the inventive polymers can combine low cold flow values, good processing characteristics of the corresponding tyre tread compositions and good tyre tread properties of the corresponding vulcanizates.

The inventive polymers 1b and 1c in the test series 1a-e have much higher ML values compared to the comparative polymers in this series.

The comparative polymers of the test series 5a, 5c, 5d and 5e also have high ML values and hence low cold flow values. Rubber mixtures comprising these comparative polymers of the test series 5a-e, however, show poorer dynamic properties (5a, 5c) or poorer processing characteristics (5d, 5e). Thus, the inventive polymers or rubber mixtures thereof combine low cold flow, good dynamic properties and good processing characteristics.

What is claimed is:

1. A polymer mixture comprising:
   a) cold-flow reduced, end group functionalized polymers comprising a polymer chain terminated by at least one sane-containing carboxyl group of the formula (I)

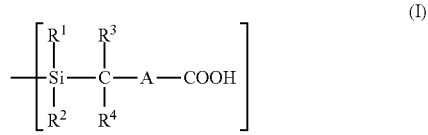

where
   R¹, R² are the same or different and are each an H, alkyl, alkoxy, cycloalkyl, cycloalkoxy, aryl, aryloxy, alkaryl, alkaryloxy, aralkyl, or aralkoxy radical, R³, R⁴ are the same or different and are each an H, alkyl, cycloalkyl, aryl, alkaryl or aralkyl radical, and
   A is a divalent organic radical wherein the polymers are diene polymers or diene copolymers; and
   b) dimers having one or more structural elements derived from silalactones of the formula (III),

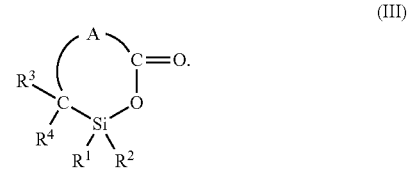

2. The polymer mixture according to claim 1, wherein the polymer is obtained by reaction of reactive ends of the polymer chain with one or more silalactone functionalizing reagents wherein the silalactones are compounds of the formula (III)

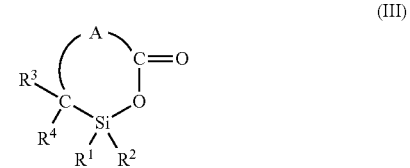

3. The polymer mixture according to claim 1, wherein:
   the polymer is obtained by reaction of reactive ends of the polymer chain with one or more silalactones of the formula (III)

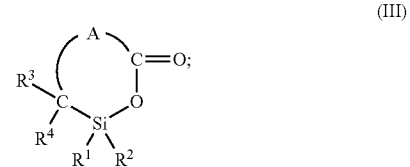

the polymers comprise at least one of polybutadiene, polyisoprene, butadiene-isoprene copolymer, butadiene-styrene copolymer, isoprene-styrene copolymer, and butadiene-isoprene-styrene terpolymer;
   R¹ and R² are the same or different and are each an H, $(C_1$-$C_{24})$-alkyl, $(C_1$-$C_{24})$-alkoxy, $(C_3$-$C_{24})$-cycloalkyl, ($C_3$-$C_{24}$)-cycloalkoxy, ($C_6$-$C_{24}$)-aryl, ($C_6$-$C_{24}$)-aryloxy, ($C_6$-$C_{24}$-alkaryl, ($C_6$-$C_{24}$)-alkaryloxy, ($C_6$-$C_{24}$)-aralkyl or ($C_6$-$C_{24}$)-aralkoxy radical; and $R^3$ and $R^4$ are the same or different and are each an H, ($C_1$-$C_{24}$)-alkyl, ($C_3$-$C_{24}$)cycloalkyl, ($C_6$-$C_4$)-aryl, ($C_6$-$C_{24}$)-alkaryl or ($C_6$-$C_{24}$)-aralkyl radical.

4. The polymer mixture according to claim 3, wherein any alkyl, alkoxy, cycloalkyl, cycloalkoxy, aryl, aryloxy, alkaryl, alkaryloxy, aralkyl, aralkoxy, or divalent organic radical may contain one or more heteroatoms selected from the group consisting of O, N, S and Si.

5. The polymer mixture according to claim 4, wherein:
the silalactones comprise one or more of 2,2-dimethyl-1-oxa-2-silacyclohexan-6-one, 2,2,4-trimethyl-1-oxa-2-silacyclohexan-6-one, 2,2,5-trimethyl-1-oxa-2-silacyclohexan-6-one, 2,2,4,5-tetramethyl-1-oxa-2-silacyclohexan-6-one, 2,2-diethyl-1-oxa-2-silacyclohexan-6-one, 2,2-diethoxy-1-oxa-2-silacyclohexan-6-one, 2,2-dimethyl-1,4-dioxa-2-silacyclohexan-6-one, 2,2,5-trimethyl-1,4-dioxa-2-silacyclohexan-6-one, 2,2,3,3-tetramethyl-1,4-dioxa-2-silacyclohexan-6-one, 2,2-dimethyl-1-oxa-4-thia-2-silacyclohexan-6-one, 2,2-diethyl-1-oxa-4-thia-2-silacyclohexan-6-one, 2,2-dphenyl-1-oxa-4-thia-2-silacyclohexan-6-one, 2-methyl-2-ethenyl-1-oxa-4-thia-2-silacyclohexan-6-one, 2,2,5-trimethyl-1-oxa-4-thia-2-silacyclohexan-6-one, 2,2-dimethyl-1-oxa-4-aza-2-silacyclohexan-6-one, 2,2,4-trimethyl-1-oxa-4-aza-2-silacyclohexan-6-one, 2,4-dimethyl-2-phenyl-1-oxa-4-aza-2-silacyclohexan-6-one, 2,2-dimethyl-4-trimethylsilyl-1-oxa-4-aza-2-silacyclohexan-6-one, 2,2-diethoxy-4-methy-1-oxa-4-aza-2-silacyclohexan-6-one, 2,2,4,4-tetramethyl-1-oxa-2,4-disilacyclohexan-6-one, 3,4-dihydro-3,3-dimethyl-1H-2,3-benzoxasilin-1-one, 2,2-dimethyl-1-oxa-2-silacyclopentan-5-one, 2,2,3-trimethyl-1-oxa-2-silacyclopentan-5-one, 2,2-dimethyl-4-phenyl-1-oxa-2-silacyclopentan-5-one, 2,2-di(tert-butyl)-1-oxa-2-silacyclopentan-5-one, 2-methyl-2-(2-propen-1-yl)-1-oxa-2-silacyclopentan-5-one, 1,1-dimethyl-2,1-benzoxasilol-3(1H)-one, and 2,2-dimethyl-1-oxa-2-silacyclohexan-7-one; and
the polymer is at least one of 1,3-butadiene, isoprene, a copolymer of 1,3-butadiene and styrene, and a copolymer of isoprene and styrene, and the polymers have n mean molar masses of 100,000 to 1,000,000 g/mol, and glass transition temperatures of −110° C. to 0° C.

6. The polymer mixture according to claim 1, wherein the one or more structural elements derived from silalactones is a structural element of the formula (IV)

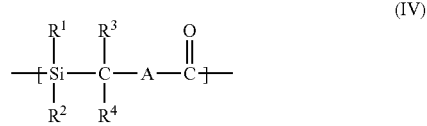

interconnecting two polymers via chain ends of the polymers.

7. The polymer mixtures according to claim 1, wherein the polymers have mean molar masses of 10,000 to 2,000,000 g/mol.

8. The polymer mixtures according to claim 7, wherein the polymers have glass transition temperatures of −110° C. to +20° C.

9. A process for preparing end group-functionalized polymers comprising a polymer chain terminated by at least one silane-containing carboxyl group of the formula (I)

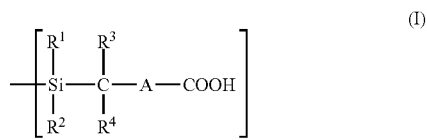

where
$R^1$, $R^2$ are the same or different and are each an H, alkyl, alkoxy, cycloalkyl, cycloalkoxy, aryl, aryloxy, alkaryl, alkaryloxy, aralkyl, or aralkoxy radical,
$R^3$, $R^4$ are the same or different and are each an H, alkyl, cycloalkyl, aryl, alkaryl or aralkyl radical, and
A is a divalent organic radical;
the process comprising contacting polymers with 0.005 to 2% by weight of one or more silalactones based on the amount of the polymer, to produce end group-functionalized polymers.

10. Vulcanizable rubber compositions comprising:
a) a polymer mixture according to claim 1; and
b) ageing stabilizers, oils, fillers, rubbers and/or further rubber auxiliaries.

11. Mouldings produced from vulcanizable rubber compositions according to claim 10.

* * * * *